US007977356B2

(12) United States Patent
Grimler et al.

(10) Patent No.: US 7,977,356 B2
(45) Date of Patent: Jul. 12, 2011

(54) OPTICAL ISOMERS OF AN ILOPERIDONE METABOLITE

(75) Inventors: Dominique Grimler, Hirsingue (FR); Hans O. Kalkman, Basel (CH); Hequn Yin, Basking Ridge, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/403,755

(22) Filed: Mar. 13, 2009

(65) Prior Publication Data

US 2009/0176739 A1    Jul. 9, 2009

Related U.S. Application Data

(63) Continuation of application No. 10/488,128, filed on Sep. 16, 2004, now abandoned.

(51) Int. Cl.
*A61K 31/445*    (2006.01)
*C07D 413/04*    (2006.01)

(52) U.S. Cl. ...................................... 514/321; 546/198
(58) Field of Classification Search .................. 514/321; 546/198
See application file for complete search history.

(56) References Cited

U.S. PATENT DOCUMENTS

| 4,804,663 | A | | 2/1989 | Kennis et al. | |
|---|---|---|---|---|---|
| 5,158,952 | A | | 10/1992 | Janssen et al. | |
| 5,364,866 | A | * | 11/1994 | Strupczewski et al. | ....... 514/321 |
| 2004/0204401 | A1 | | 10/2004 | Migaly | |

FOREIGN PATENT DOCUMENTS

| EP | 402644 B1 | 8/1995 |
|---|---|---|
| JP | H03-63263 A | 3/1991 |
| JP | H09-511215 A | 11/1997 |

OTHER PUBLICATIONS

Caccia "Biotransformation of post . . ." Clin. Pharmacokinet. v. 38(6) p. 393-414 (2000).*
Corbett et al. "Iloperidone: preclinical profile . . ." Drug Rev. v.3(2) p. 120-147 (1997).*
Subramanian et al. "Receptor profile of P88 . . . " Prog. Neuro-Psychophram. Biol. Psy. v.26 p. 553-560 (2002).*
Imamura et al. "Interactions . . . " CA 102:214444(1985).*
Ookawa et al. "Antitumor complexes . . . " CA 120:62270 (1994).*
Garattini "Active drug metabolites . . . " Clin. Pharmacokinet. v.10, p. 216-227 (1985).*
Strupczewski, J.T. et al. 3-(Arylozy) Alkylpiperidinyl-1,2-Benziosoxazoles as D2/5-HT2 Antagonists with Potential Atypical Antipsychotic Activity: Antipsychotic Profile of Iloperidone (HP 873), Journal of Medicinal Chemistry, vol. 38, No. 7, pp. 1119-1131, 1995.
Subramanian, N. et al., "Receptor profile of P88-8991 and P95-12113, metabolites of the novel antipsychotic iloperidone," Progress in Neuro-Psychopharmacology & Biological Psychiatry, 26:553-560, 2002.
64 USPQ2d 1032 Decided Aug. 2002.
Corey E. J. et al., "A Stable and Easily Prepared Catalyst for the Enantioselective Reduction of Ketones. Applications to Multistep Syntheses", Journal of the American Chemical Society, vol. 109, No. 25, pp. 7925-7926, 1987.
Mutlib, A.E. et al., "Application of Liquid Chromatography/Mass Spectrometry in Accelerating the Identification of Human Liver Cytochrome P450 Isoforms Involved in the Metabolism of Iloperidone", The Journal of Pharmacology and Experimental Theraputics, vol. 286, No. 3 pp. 1285-1293.
Mutlib, A.E. et al., "Picogram determination of iloperidone in human plasma by solid-phase extraction and by high-performance liquid chromatography-selected-ion monitoring electrospray mass spectrometry", Journal of Chromatography B. 669, 1995, pp. 237-246.
Meltzer, H., "The Role of Serotonin an Antipsychotic Drug Action", Neuropsyhopharmacology, vol. 21, No. 2S, 1999.
Williams et al., "Importance of Drug Enantiomers in Clinical Pharmacology", Department of Clinical Pharmacology, St. Vincent's Hospital, Darlinghurst, Sydney, Drugs 30, 1985, pp. 333-354.
Kuntzelmann, "Functional characterization of the enantiomers of P88-8991 at the human a2c adrenoceptor and the human dopamine D2A receptor", Novartis Pharma AG report, Sep. 27, 2001, 8 pages.
Neumann, "The effect of the enantiomers of P88-8991 in ilperidone on spontaneous locomotion and amphetamine-induced locomotion in rats" Novartis Pharma AG report, Sep. 27, 2001, 10 pages.
Fura, Aberra, "Role of pharmacologically active metabolites in drug discovery and development", Drug Discovery Today, Feb. 2006, 11(3/4): 133-142.
Clarke, Frank H., "Role of Drug Metabolism in Drug Research and Development: View of a Medicinal Chemist", Journal of Pharmaceutical Sciences, 1678.
Blumer et al., "NVP-AES059-NX1 and NVP-AES060-NX-1; Enantiomers of the P88 8991 metabolite of Iloperidone: Receptor Affinity Profile (Short List)", Novartis Pharma AG report, Jan. 28, 2001, 10 pages.
Grimler et al., U.S. Appl. No. 10/488,128, 4-32076A, Office Action Communication, Mar. 16, 2006, 8 pages.
Grimler et al., U.S. Appl. No. 10/488,128, 4-32076A, Office Action Communication, Sep. 25, 2006, 7 pages.
Grimler et al., U.S. Appl. No. 10/488,128, 4-32076A, Office Action Communication, Jun. 14, 2007, 8 pages.
Grimler et al., U.S. Appl. No. 10/488,128, 4-32076A, Office Action Communication, Mar. 6, 2008, 9 pages.
Grimler et al., U.S. Appl. No. 10/488,128, 4-32076A, Office Action Communication, Oct. 17, 2008, 13 pages.
Grimler et al, U.S. Appl. No. 60/316,390, PV Application, Aug. 31, 2001.
Nozulak et al., U.S. Appl. No. 10/575,040, filed Dec. 6, 2006, Office Communication dated May 5, 2010, 7 pages.
Waller et al., Prodrugs, 1989, pp. 497-507, Br. J. Clin. Pharmac, vol. 28.
Bundgaard, "Design of Prodrugs", 1985, pp. 1-3, Elsevier Science Publishers B.V.

* cited by examiner

*Primary Examiner* — Celia Chang
(74) *Attorney, Agent, or Firm* — Hoffman Warnick LLC

(57) ABSTRACT

The present invention relates to novel isomers of a metabolite of Iloperidone, their preparation, their use as pharmaceuticals and pharmaceutical compositions containing them.

10 Claims, No Drawings

OPTICAL ISOMERS OF AN ILOPERIDONE METABOLITE

CROSS-REFERENCE TO RELATED APPLICATIONS

This application is a continuation of U.S. patent application Ser. No. 10/488,128, filed 16 Sep. 2004 now abandoned, which is hereby incorporated herein.

The present invention relates to novel isomers of a metabolite of Iloperidone, their preparation, their use as pharmaceuticals and pharmaceutical compositions containing them.

More particularly, the invention relates to optical isomers of the metabolite P-88-8991 of Iloperidone.

Iloperidone is an atypical antipsychotic developed for the treatment of schizophrenia, having functional affinity for noradrenergic, dopaminergic and serotoninergic receptors. See for example Richelson E. and Souder T, Life Sciences, 68:29-39 (2000).

P-88-8991 is a major circulating metabolite of Iloperidone in human plasma, having the formula A

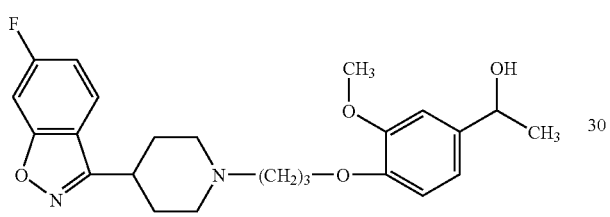

A

See for example Mutlib A E et al., Drug Metab. Dispos; 23(9):951-964 (1995). P-88-8991 has been shown to have plasma levels in human about 1.5 fold higher than the parent drug. It is roughly as active as Iloperidone.

P-88-8991 consists of a mixture of two enantiomers which have never been disclosed in the literature. It has now surprisingly been found that humans produce only one enantiomer stereospecifically following administration of Iloperidone.

In the first aspect, the invention provides the enantiomers (R)-P-88-8991 and (S)-P-88-8991 of formulae I and II

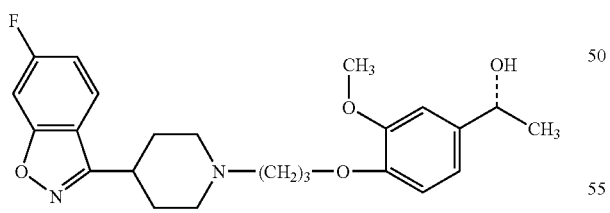

I

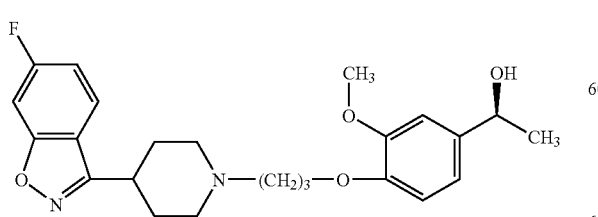

II in free base or acid addition salt form.

In a further aspect, the invention provides a process for the production of the compounds of formulae I and II, comprising the reduction of Iloperidone of formula III

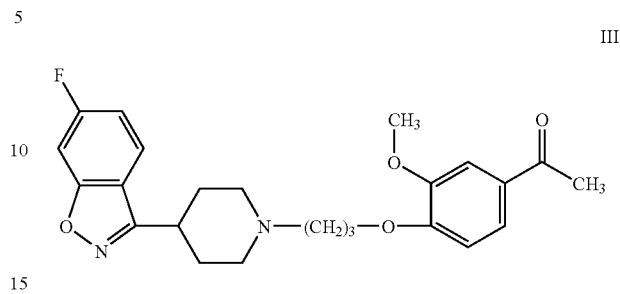

III with an optically active boran complex of formula IV

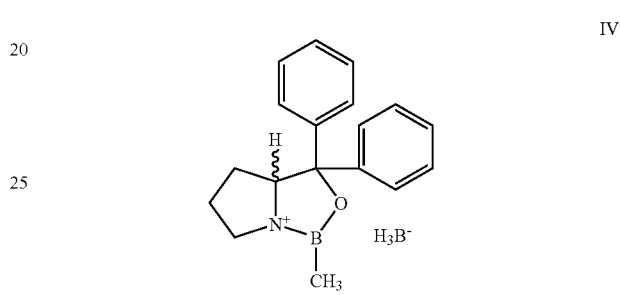

IV

The compound (S)-1-(4-{3-[4-(6-fluoro-benzo[d]isoxazol-3-yl)-piperidin-1-yl]-propoxy}-3-methoxy-phenyl)-ethanol of formula I is obtained using the boran complex of (3aR,7R}-1-methyl-3,3-diphenyl-tetrahydro-pyrrolo[1,2-c][1,3,2]oxazaborole of formula IVa

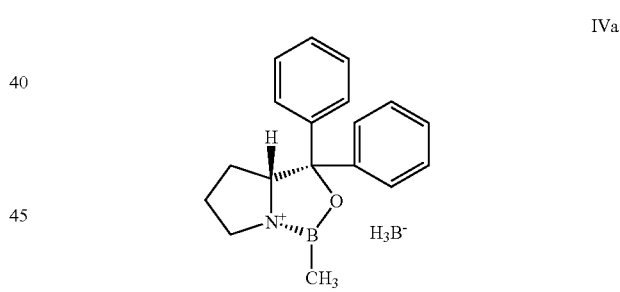

IVa whereas the compound (R)-1-(4-{3-[4-(6-fluoro-benzo[d]isoxazol-3-yl)-piperidin-1-yl]propoxy}-3-methoxyphenyl}ethanol of formula II is obtained using the boran complex of (3aS,7R)-1-methyl-3,3-diphenyl-tetrahydro-pyrrolo[1,2-c][1,3,2]oxazaborole of formula IVb

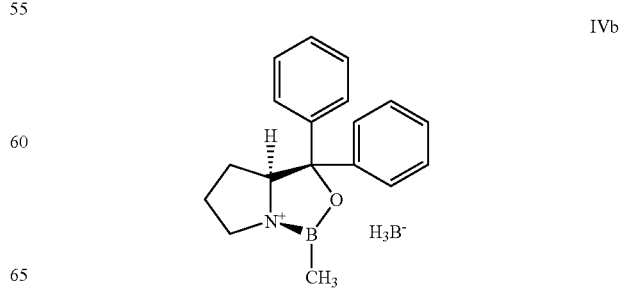

IVb

The reactions can be effected according to conventional methods, e.g. as described in the Examples.

Working up the reaction mixtures and purification of the compounds thus obtained may be carried out in accordance to known procedures.

Acid addition salts may be produced from the free bases in known manner, and vice-versa. Suitable acid addition salts for use in accordance with the present invention include for example the hydrochloride.

The boran complexes used as starting materials can be produced from the corresponding compounds of formula Va and Vb

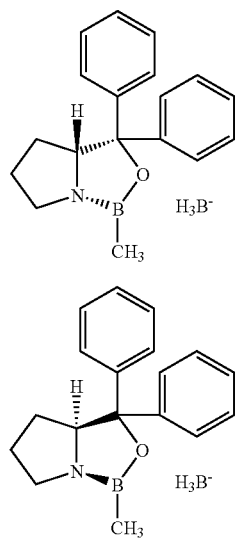

according to known procedures, e.g. as described in the Examples.

The starting materials of formulae Va and Vb are known.

The compounds of formulae I and II and their pharmaceutically acceptable acid addition salts, hereinafter referred to as agents of the invention, exhibit valuable pharmacological properties when tested in vitro and in animals, and are therefore useful as pharmaceuticals.

In particular the agents of the invention display high affinity for adrenergic $\alpha_1$ and $\alpha_{2c}$ receptors ($pK_i$ 8.9 and 7.8 respectively, for the compound of formula I, and 9.2 and 7.7 respectively, for the compound of formula II), high affinity for $5HT_{2A}$ and $5HT_6$ receptors ($pK_i$ 8.9 and 8.1 respectively, for the compound of formula I, and 8.9 and 7.8 respectively, for the compound of formula II) and moderate affinity for the $D_2$ family ($pK_i$ 7.4 to 7.6 for the compound of formula I and 7.4 to 7.8 for the compound of formula II).

Receptor affinity is determined with standard radioligand binding techniques, using human recombinant receptors and native rat brain receptors. Blockade of dopamine $D_2$ and noradrenergic $\alpha_{2c}$ receptors is tested in cell-lines using luciferase reporter gene assays based on 2nd messenger responses.

In vivo, the agents of the invention exhibit antipsychotic activity, as assessed in standard tests such as the amphetamine-induced hypermotility and the phencyclidine-induced hyperlocomotion tests.

The amphetamine-induced hypermotility test is performed according to the method described by Arnt J in Eur. J. Pharmacol. 283, 55-62 (1995). In this test, the agents of the invention significantly inhibit the amphetamine-induced locomotion of the animals at doses of about 0.01 to about 10 mg/kg s.c.

The phencyclidine-induced hyperlocomotion test is performed according to a rat adaptation of the method described by Gleason S D and Shannon H E in Psychopharmacol. 129, 79-84 (1997). In this test, the agents of the invention significantly block the phencyclidine-induced hyperlocomotion of the rats at doses of about 0.01 to about 10 mg/kg s.c.

The agents of the invention are therefore useful for the treatment of psychotic disorders such as schizophrenia and bipolar disorders.

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 500, preferably from about 0.5 to about 100 mg/kg animal body weight. In larger mammals, for example humans, an indicated daily dosage is in the range from about 1 to about 500, preferably from about 1 to about 300 mg of an agent of the invention, conveniently administered, for example, in divided doses up to four times a day or in sustained release form.

The agent of the invention may be administered by any conventional route, in particular enterally, preferably orally, for example in the form of tablets or capsules, or parenterally, for example in the form of injectable solutions or suspensions.

The agents of the invention may alternatively be administered e.g. topically in the form of a cream, gel or the like, or by inhalation, e.g. in dry powder form.

Examples for compositions comprising an agent of the invention include, e.g. a solid dispersion, an aqueous solution, e.g. containing a solubilising agent, a microemulsion and a suspension of an agent of the invention. The composition may be buffered to a pH in the range of e.g. from 3.5 to 9.5, by a suitable buffer.

The agents of the invention can be administered either alone or in combination with other pharmaceutical agents effective in the treatment of psychotic disorders such as schizophrenia or bipolar disorders. The present invention thus provides a combination comprising a therapeutically effective amount of an agent of the invention and a second drug substance, for simultaneous or sequential administration.

In accordance with the foregoing, the present invention also provides an agent of the invention, for use as a pharmaceutical, e.g. for the treatment of psychotic disorders.

The present invention furthermore provides a pharmaceutical composition comprising an agent of the invention in association with at least one pharmaceutical carrier or diluent. Such compositions may be manufactured in conventional manner. Unit dosage forms contain, for example, from about 0.25 to about 150, preferably from 0.25 to about 25 mg of a compound according to the invention.

Moreover the present invention provides the use of an agent of the invention, for the manufacture of a medicament for the treatment of psychotic disorders.

In still a further aspect the present invention provides a method for the treatment of psychotic disorders in a subject in need of such treatment, which comprises administering to such subject a therapeutically effective amount of an agent of the invention.

The following examples illustrate the invention.

EXAMPLE 1

(S)-1-[4-{3-[4-(6-Fluoro-benzo[d]isoxazol-3-yl)-piperidin-1-yl]-propoxy}-3-methoxy-phenyl)ethanol 56.36 g of boran complex of (3aR,7R)-1-methyl-3,3-diphenyl-tetrahydropyrrolo[1,2c][1,3,2]oxazaborole (1 equivalent) is dissolved under nitrogen in methylenehloride, and the solution is cooled to 0° C. A 1M solution of 1-(4-{3-[4-(6-fluoro-benzo[d]isoxazol-3-yl)piperidin-1-yl]-propoxy}-3-methoxy-phenyl)-ethanone (Iloperidone; 1 equivalent) in methylenehloride is added via a dropping funnel over 90 minutes while the internal temperature is maintained at 0° C.±2° C. After the addition is complete, the mixture is stirred at 0° C. for 20 hours. The reaction mixture is then poured into precooled methanol (0-5° C.) during 1 hour. The solution is warmed to room temperature and stirred until the $H_2$ evolution ceases. The solution is concentrated by distillation and the residue dried in vacuum, treated with methanol and stirred for about 1 hour at 50° C. and an additional hour at 0° C. The product is isolated by filtration and dried under reduced pressure for 3 hours at 50° C. The title compound is obtained (white crystals).

$[\alpha]_D^{20}$ −19.3° (c=1 in chloroform)

Mp: 138.2-138.8° C.

The boran complex used as starting material can be obtained as follows:

200 mL of a solution of (3aR,7R)-1-methyl-3,3-diphenyl-tetrahydro-pyrrolo[1,2c][1,3,2]oxazaborole (1M in toluene) is stirred at room temperature under nitrogen. 1.2 equivalent borane-dimethylsulfide complex is added with a syringe. The solution is stirred for 2 further hours at room temperature. The borane complex is then crystallised by addition of 4 vol dry hexane and cooling to −12° C. for 1.5 hour. The product is isolated by filtration in a sintered glass funnel and dried in vacuum at 40° C. The boran complex is obtained (white crystals).

EXAMPLE 2

(R)-1-(4-{3-[4-(6-fluoro-benzo[d]isoxazol-3-yl]-piperidin-1-yl]-propoxy}-3-methoxy-phenlyl)ethanol This compound is produced in analogy to Example 1, using boran complex of (3aS,7R)-1-methyl-3,3-diphenyl-tetrahydro-pyrrolo[1,2-c][1,3,2]oxazaborole.

$[\alpha]_D^{20}$=+18.4° (c=1 in chloroform)

Mp: 137.9-138.3° C.

What is claimed is:

1. A pharmaceutical composition, in the form of capsules, tablets, or injectable solutions or suspensions, for use as a pharmaceutical in the treatment of a psychotic disorder in a human consisting essentially of an antipsychotic effective amount of (S)-1-[4-{3-[4-(6-fluoro-benzo(d)isoxazol-3-yl)-piperidin-1-yl]propoxy}-3-methoxy-phenyl]-ethanol or a pharmaceutically acceptable salt thereof and a pharmaceutical carrier or diluent.

2. The pharmaceutical composition of claim 1 for treating a psychotic disorder in a human consisting essentially of an antipsychotic effective amount of (S)-1-[4-{3-[4-(6-fluoro-benzo(d)isoxazol-3-yl)-piperidin-1-yl]propoxy}-3-methoxy-phenyl]-ethanol prepared by enantioselective reduction of iloperidone and a pharmaceutical carrier or diluent.

3. The pharmaceutical composition of claim 2, wherein the reduction is effected by contact of iloperidone with an optically-active borane complex of formula IV

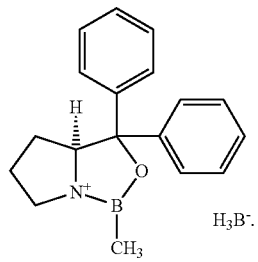

IV

4. The pharmaceutical composition of claim 1 in the form of a capsule or tablet.

5. The pharmaceutical composition of claim 1 in the form of a capsule, tablet, or injectable solution or suspension consisting essentially of about 1 to about 500 mg of (S)-1-[4-{3-[4-(6-fluoro-benzo(d)isoxazol-3-yl)-piperidin-1-yl]propoxy}-3-methoxy-phenyl]-ethanol and a pharmaceutical carrier or diluent.

6. The pharmaceutical composition of claim 1 in unit dosage form consisting essentially of 0.25 to about 25 mg of (S)-1-[4-{3-[4-(6-fluoro-benzo(d)isoxazol-3yl)-piperidin-1-yl]propoxyl}-3-methoxy-phenyl]-ethanol and a pharmaceutical carrier or diluent.

7. A method for treating a psychotic disorder in a human subject in need of such treatment, the method comprising orally or parenterally administering to the subject a therapeutically effective amount of (S)-1-[4-{3-[4-(6-fluoro-benzold(d)isoxazol-3-yl)-piperidin-1-yl]propoxy}-3-methoxy-phenyl]-ethanol or a pharmaceutically acceptable salt thereof admixed with at least one pharmaceutical carrier.

8. The method of claim 7, wherein the pharmaceutical composition is in the form of a capsule or tablet.

9. The method of claim 7, wherein the pharmaceutical composition is in the form of a capsule, tablet, or injectable solution or suspension consisting essentially of about 1 to about 500 mg of (S)-1-[4-{3-[4-(6-fluoro-benzo(d)isoxazol-3-yl)piperidin-1-yl]propoxy}-3-methoxy-phenyl]-ethanol and a pharmaceutical carrier or diluent.

10. The method of claim 7, wherein the pharmaceutical composition is in unit dosage form consisting essentially of 0.25 to about 25 mg of (s)-1-[4-{3-[4-(6-fluoro-benzo(d)isoxazol-3-yl)-piperidin-1-yl]propoxy}-3-methoxy-phenyl]-ethanol and a pharmaceutical carrier or diluent.

* * * * *